(12) United States Patent
Foreman

(10) Patent No.: US 7,672,802 B2
(45) Date of Patent: Mar. 2, 2010

(54) APPARATUS AND METHOD FOR CALIBRATING EARPHONES FOR AUDIOMETRIC TESTING

(75) Inventor: Jack Foreman, Pflugerville, TX (US)

(73) Assignee: Diagnostic Group, LLC, Eden Prairie, MN (US)

( * ) Notice: Subject to any disclaimer, the term of this patent is extended or adjusted under 35 U.S.C. 154(b) by 68 days.

(21) Appl. No.: 11/897,216

(22) Filed: Aug. 29, 2007

(65) Prior Publication Data

US 2009/0063080 A1 Mar. 5, 2009

(51) Int. Cl.
*G01K 11/00* (2006.01)

(52) U.S. Cl. .................................................. 702/103
(58) Field of Classification Search .................. 702/85, 702/103; 381/58, 371; 704/225, 226
See application file for complete search history.

(56) References Cited

U.S. PATENT DOCUMENTS

| 4,038,496 | A | * | 7/1977 | Feezor | ........................ 73/585 |
| 6,468,224 | B1 | | 10/2002 | Foreman et al. | |
| 2003/0065276 | A1 | * | 4/2003 | Akita | ......................... 600/559 |

* cited by examiner

*Primary Examiner*—Bryan Bui
(74) *Attorney, Agent, or Firm*—Kinney & Lange, P.A.

(57) ABSTRACT

A system and method for performing audiometric testing utilizes an independently normalized audiometer and independently calibrated earphones.

12 Claims, 2 Drawing Sheets

APPARATUS AND METHOD FOR CALIBRATING EARPHONES FOR AUDIOMETRIC TESTING

BACKGROUND

The present invention relates to an apparatus and method for calibrating earphones for audiometric testing, and more particularly to a system for separately calibrating audiometers to produce a normalized output and earphones according to an objective standard, so that any independently calibrated earphones may be used with any audiometer.

Audiometers are used to test the hearing capabilities of individuals. An audiometric test is performed by operating an audiometer to present precise audible tones or other stimulus to a test subject by acoustic transducers such as earphones. The test subject indicates whether the tones have been heard by an input mechanism such as a handswitch.

The earphones are typically either connected directly to the audiometer by use of industry standard stereo jacks or through the wall of a sound room by such stereo jacks connected to the audiometer. Earphones may include two wires and two stereo plugs, one for the each ear. A problem can arise if the two stereo plugs associated with the earphones are inserted into incorrect stereo jacks of the audiometer, for example if the left ear stereo plug is inserted into the right ear stereo jack of the audiometer. Extreme care is required to assure that earphones plugs are inserted properly into an audiometer before testing is conducted.

In addition, earphones traditionally are calibrated for a specific audiometer to which they are connected. That is, earphones can only be considered to be properly calibrated and ready for use if they are connected to the specific audiometer for which they had been calibrated. Earphones may not be used interchangeably with multiple audiometers. It is therefore very important to ensure that certain earphones are used with only certain audiometers so that valid audiometric test results are obtained.

The level of care that must be taken to assure that earphones are connected properly to an audiometer, and that earphones are only connected to a certain audiometer for which they are calibrated, requires significant administration and oversight. This increases the cost of operating and maintaining an audiometric testing facility. U.S. Pat. No. 6,468,224 describes a calibrated audiometer system that utilizes integrated circuit chips embedded in the plugs associated with the earphones and the handswitch, allowing identification information to be obtained to confirm that the headphones are being used with a correct audiometer and that the headphones are plugged into the proper jacks of the audiometer. It would be of further use in the art to provide an improved system and method for calibrating earphones for performing audiometric testing, so that any calibrated earphones may be used with any normalized audiometer.

SUMMARY

The present invention is a method and system for performing audiometric testing utilizing an independently normalized audiometer and independently calibrated earphones.

DETAILED DESCRIPTION

Figure 1:
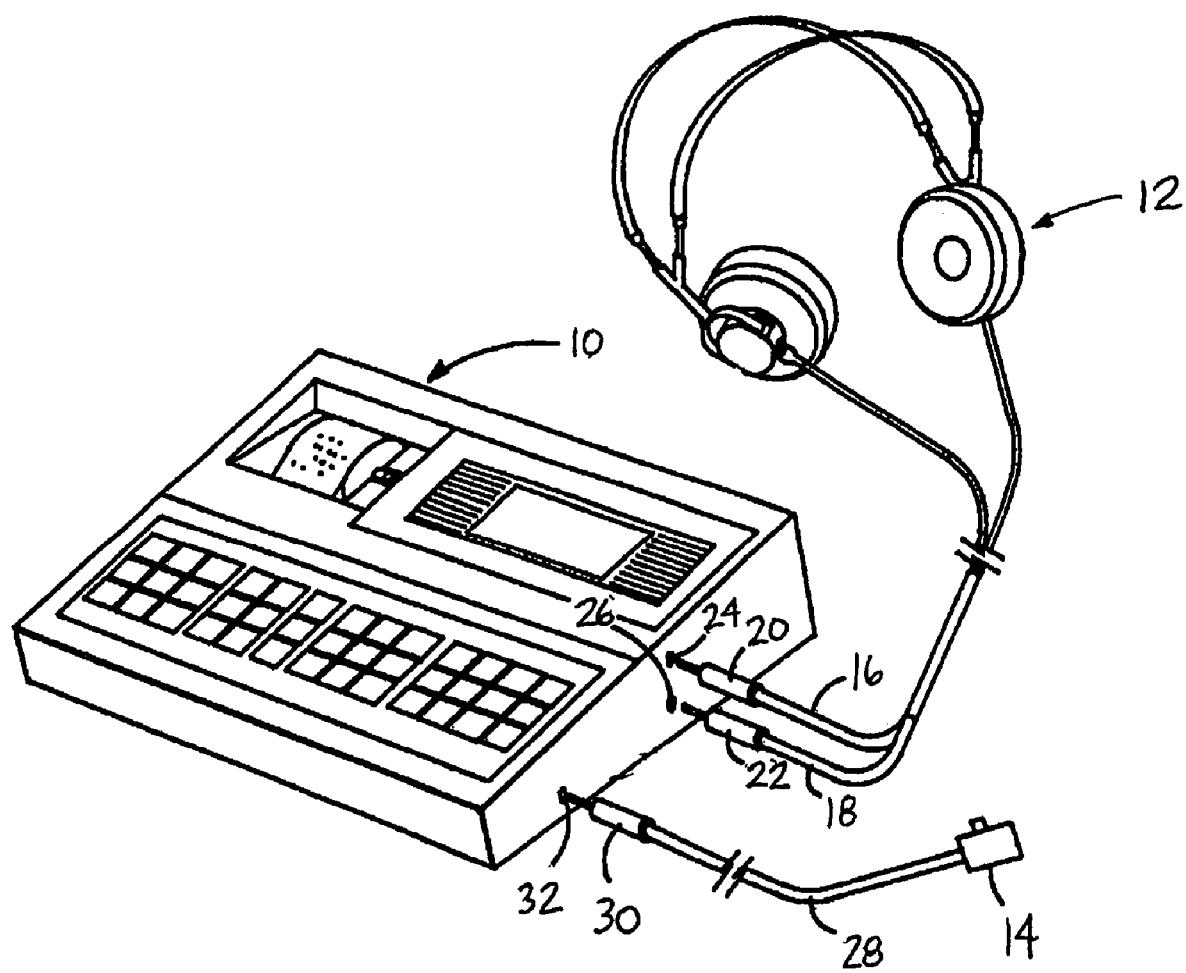
FIG. 1 is a diagram illustrating an audiometer having earphones and a handswitch connected thereto for performing an audiometric hearing test.

FIG. 1 is a diagram illustrating audiometer 10 having earphones 12 and handswitch 14 connected thereto for performing an audiometric hearing test. Earphones 12 are connected to audiometer 10 via cables 16 and 18 with plugs 20 and 22 adapted to be inserted into corresponding jacks 24 and 26, respectively. Handswitch 14 is connected to audiometer 10 via cable 28 with plug 30 adapted to be inserted into jack 32. Audiometer 10, which may be a stand-alone device, may cooperate with a computer (not shown), or may be incorporated into a computer in various embodiments, is operable to perform pure-tone hearing threshold testing in accordance with accepted audiometric procedures. Earphones 12 include integrated circuit chips (not visible in FIG. 1) located inside plugs' 20 and 22 for storing calibration information and other information, as will be discussed in detail below.

The components described above and shown in FIG. 1 are in many ways similar to those described in U.S. Pat. No. 6,468,224, and that patent is therefore incorporated by reference herein to further explain these components. It should be noted that in addition to the DS2401 Silicon Serial Number Chip sold by Maxim/Dallas Semiconductor, Dallas, Tex. noted in U.S. Pat. No. 6,468,224, the present invention may also employ DS2431 chips also sold by Maxim/Dallas Semiconductor.

Figure 2:
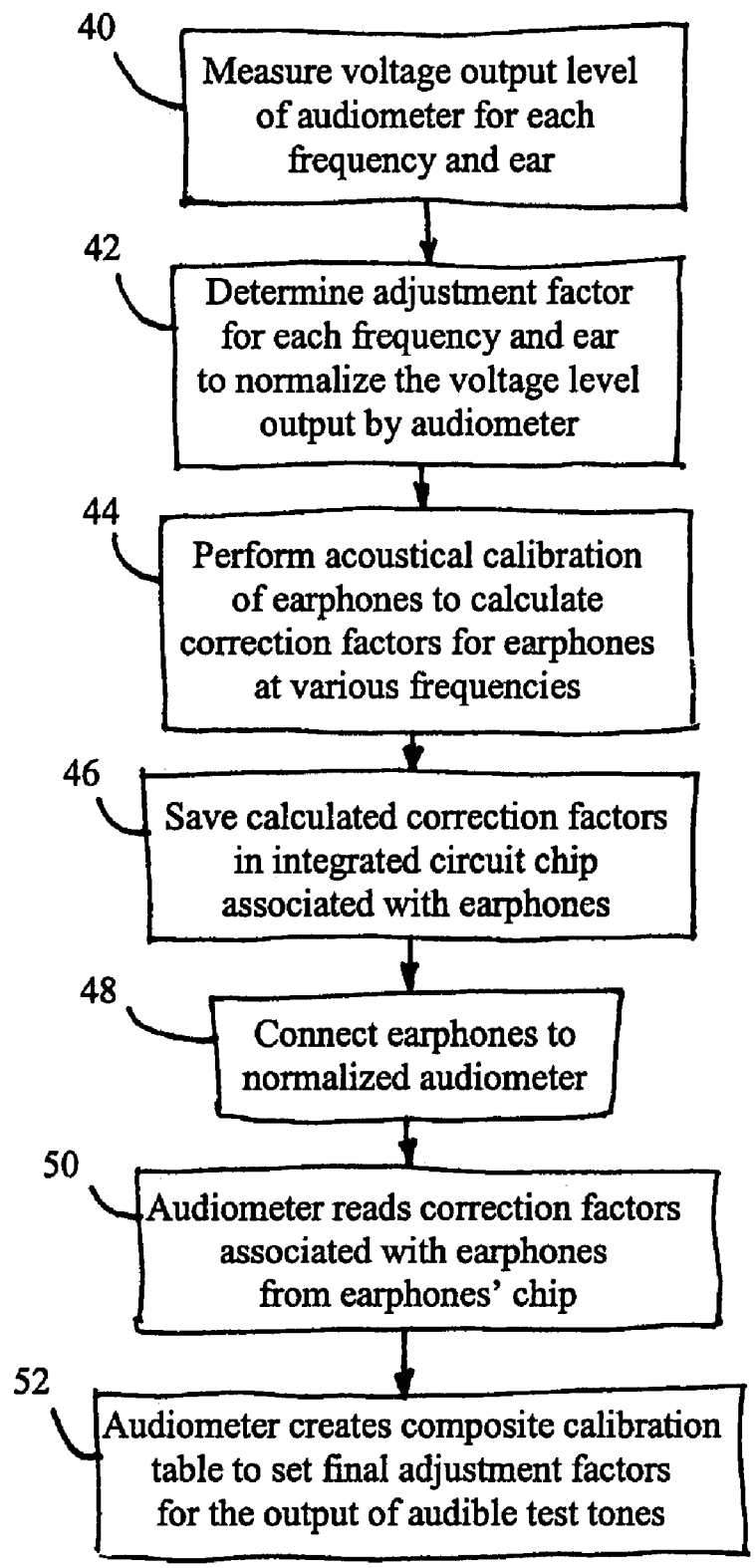
FIG. 2 is a flow diagram illustrating a process for calibrating earphones according to an embodiment of the present invention, so that any calibrated earphones may be used with any normalized audiometer.

FIG. 2 is a flow diagram illustrating a process for calibrating earphones according to an embodiment of the present invention, so that any calibrated earphones may be used with any normalized audiometer. First, at step 40, the voltage output level of an audiometer is measured for each frequency and ear. An adjustment factor is then determined at step 42 for each frequency and ear, in order to normalize the voltage level output by the audiometer to a known, fixed level for each frequency and ear. As a result of this audiometer normalization, it is assured that all audiometers have consistent electrical voltage output levels. Acoustical calibration of earphones is then performed as indicated by step 44 in order to calculate a correction factor for the earphones at various frequencies. This acoustical calibration is performed independently of a particular audiometer, unlike prior systems which required acoustical calibration to be done with the earphones connected to a specific audiometer with which the earphones would exclusively be used. The calculated correction factors are saved in an integrated circuit chip associated with the earphones, as indicated by step 46.

Once the independent calibration procedures for the audiometer and the earphones have been completed, the earphones may be connected to any normalized audiometer, as indicated by step 48. The audiometer reads the correction factors associated with the earphones from the earphones' chip at step 50, and creates a composite calibration table at step 52 to set final adjustment factors for the output of audible test tones in an audiometric test based on both the adjustment factors associated with the audiometer and the correction factors associated with the earphones. As a result, it is possible for any normalized audiometer to cooperate with any calibrated earphones for reliable audiometric testing.

The audiometer may also read information stored in the earphones' chip(s) regarding the connection of the left and right plugs to the left and right jacks to ensure that the earphones are connected properly, as is generally described in U.S. Pat. No. 6,468,224 (which has been incorporated by reference). In addition, the earphones' integrated circuit chip(s) may store additional information, such as the revision level of the stored information (to account for the possibility of updating the normalization levels of audiometers, for example), the date of calibration of the earphones, the calibration company and technician that performed the acoustical calibration of the earphones, the serial number of the earphone assembly, or other information.

In an exemplary embodiment, the normalization of the electrical output of the audiometer (steps 40 and 42) is performed with a sound level meter (typically including an octave band filter and an NBS-9 coupler) and a signal analyzer capable of measuring an displaying frequency, total harmonic distortion, pulse width, rise and fall times, and tone overshoot. An exemplary test procedure may be performed as follows:

1. Place audiometer in Manual Mode/Pulse Mode Off.
2. Couple the Left TDH Phone to the Sound Level Meter using the NBS-9A Coupler and Weight.
3. Set the Octave Band Filter to 500 Hertz (Hz).
4. Present 70 dBHL (Hearing Level) through the Left Phone at 500 Hz.
5. Measure and record the frequency to ensure it is within 3% of expected.
6. Measure the Sound Pressure Level (SPL) output to ensure it is within 3 dB of expected.
7. Record deviations from expected values in calibration table.
8. Repeat steps 3-7 for 1000 Hz, 2000 Hz, 3000 Hz, 4000 Hz, 6000 Hz and 8000 Hz.
9. Turn off Octave Band Filter.
10. Present 110 dBHL (or highest level of output) at 500 Hz.
11. Measure and record the percentage of total harmonic distortion (THD %).
12. Repeat steps 10 and 11 for 1000 Hz, 2000 Hz, 3000 Hz and 4000 Hz.
13. Present 90 dBHL (or highest level) at 6000 Hz.
14. Measure and record THD %.
15. Repeat steps 13 and 14 for 8000 Hz.
16. Place the right TDH Phone on the NBS-9A coupler and repeat steps 3-15.
17. Enter the Calibration/Adjustment Mode of the audiometer.
18. Adjust outputs that are not within specification (within 2.5 dB).
19. Store offset correction factors in audiometer.
20. Measure and record all adjusted outputs as described in steps 1-8.
21. Place audiometer in Pulse Mode and present pulsed signal at 1000 Hz.
22. Measure and record rise time, fall time, pulse width and overshoot.
23. Turn Pulse Mode off.
24. Present a tone at 70 dB (Pulse Mode off) at 1000 Hz through the Left Phone.
25. Record output with Octave Band Filter on.
26. Reduce output by 5 dB and record output.
27. Compare recorded output level to output recorded at 70 dB. Allowable tolerance is within 1 dB of expected level.
28. Repeat steps 26 and 27 until −10 dB is reached. In noise level does not allow for acoustical measurement, electrical measurement can be used.
29. Present a tone at 70 dB (Pulse Mode off) at 1000 Hz with Octave Band Filter on.
30. Increase output by 5 dB and record output.
31. Compare recorded output level to output recorded at 70 dB. Allowable tolerance is within 1 dB of expected level.
32. Repeat steps 24-31 for the Right Phone.
33. Crossover. With the tone switch in the "ON" position, and the level set to 70 dBHL, the non-test transducer shall be at least 70 dB (either acoustical or electrical) below the corresponding test transducer.
34. On/Off Ratio—with the tone switch in the "OFF" position and the level set to 90 dBHL, the output of the transducer shall be at least 70 dB down.
35. Repeat for the other ear as described in steps 33 and 34.

The acoustical calibration of the earphones (step 44) is performed in a manner well known in the art, involving the measurement of sound pressure levels (SPLs) produced by the earphones. When the earphones are connected to the audiometer, the audiometer reads the correction factors for the earphones calculated by the acoustical calibration of the earphones. The audiometer then adjusts its offset factors based on the calculated correction factors for the earphones to create a composite calibration table to set final adjustment factors for outputting audible test tones to the earphones for audiometric testing.

The interchangeability of earphones and audiometers afforded by the present invention allows audiometric testing facility operation and maintenance processes to be changed and improved. Acoustical calibration of earphones (involving the adjustment of earphone sound pressure levels) typically requires special calibration equipment that is not readily available at an audiometric testing facility, so that a calibration technician had to transport this equipment to the testing site to perform acoustical calibration with the earphones connected to the corresponding audiometers with which they would be used. The services and travel costs of the calibration technician are relatively expensive, adding cost to the operation and maintenance of the audiometric testing facility. The present invention allows pre-calibrated earphones to be provided to audiometric testing facilities, calibrated by the earphone supplier (at the factory or other facility where the earphones are manufactured or otherwise prepared for sale). When earphones are due to be re-calibrated, the audiometric testing facility has the option of exchanging the old earphones for new pre-calibrated earphones, so that a calibration technician is not required to visit the audiometric testing facility in order to provide calibrated earphones for use with the facility's audiometers.

In group testing facilities, it can be particularly challenging to ensure that a set of earphones is only used with a particular audiometer for which it is calibrated. Test subjects are often not even cognizant of this requirement. In order to ensure that valid test results are obtained, it is necessary to employ trained administrative personnel to prevent interchange of earphones between audiometers, and also to ensure that the earphones are connected to the audiometer properly. The present invention eliminates the need for this administrative function by allowing any calibrated earphones to be used with any normalized audiometer, which will reduce expenses associated with operation of the test facility.

In traditional systems, failure of an earphone assembly requires the removal of the corresponding audiometer from service, since only one earphone assembly is properly calibrated to work with a particular audiometer. The present invention allows a failed earphone assembly to be replaced with another calibrated earphone assembly from stock, so that an audiometer's service time is not lost simply by the failure of an earphone assembly.

When pre-calibrated earphones are used, it is possible for an end user to maintain a testing facility such as a school or industrial setting by calibrating their own audiometers. For example, a user may obtain one or more pre-calibrated headphone assemblies from a supplier along with a simplified audiometer normalization verification instrument. The user can use the audiometer normalization verification instrument to verify audiometer frequency, linearity and output level. The verification information is stored in the audiometer, and the pre-calibrated earphone assembly is connected to the audiometer. Then, any old earphones (that are being replaced by the pre-calibrated earphones from the supplier) and the calibration instrument can be sent back to the supplier, and the normalized audiometer and pre-calibrated earphones are ready for use.

Current OSHA regulations require that audiometers receive exhaustive calibration every two years, with acoustical calibration every year. The complexity of acoustical calibration, which requires special equipment and a trained technician, has traditionally dictated that audiometers are calibrated every year along with the acoustical calibration. Exchanging earphones that were calibrated a year or more in the past for new pre-calibrated earphones can be done by mail, so that site visits by a trained technician do not need to occur every year.

Although the present invention has been described with reference to preferred embodiments, workers skilled in the art will recognize that changes may be made in form and detail without departing from the spirit and scope of the invention.

The invention claimed is:

1. A method of calibrating an audiometer and earphones for audiometric testing, the method comprising:
    normalizing a voltage output level of the audiometer;
    performing acoustical calibration of the earphones independent from the audiometer to calculate correction factors for a variety of frequencies;
    storing the calculated correction factors in an integrated circuit chip associated with the earphones;
    connecting the earphones to the audiometer;
    reading the calculated correction factors into the audiometer from the integrated circuit chip associated with the earphones; and
    creating a composite calibration table based on the calculated correction factors to set final adjustment factors for outputting audible test tones from the audiometer.

2. The method of claim 1, wherein acoustical calibration of the earphones is performed at the same location where the earphones are manufactured.

3. The method of claim 1, further comprising storing information related to the date and/or revision level of calibration of the earphones in the integrated circuit chip.

4. The method of claim 1, further comprising storing information related to where and/or by whom the acoustical calibration of the earphones was performed.

5. The method of claim 1, further comprising storing left and right earphone information in the integrated circuit chip to ensure proper connection of the earphones to the audiometer.

6. The method of claim 1, further comprising storing serial number information related to the earphones in the integrated circuit chip.

7. A method of replacing earphones for use with an audiometer for audiometric testing, comprising:
    initially performing a method of calibrating the audiometer for use with a first set of earphones that comprises:
        normalizing a voltage output level of the audiometer;
        performing acoustical calibration of the first set of earphones independent from the audiometer to calculate correction factors for the first set of earphones for a variety of frequencies;
        storing the calculated correction factors for the first set of earphones in an integrated circuit chip associated with the first set of earphones;
        connecting the first set of earphones to the audiometer;
        reading the calculated correction factors for the first set of earphones into the audiometer from the integrated circuit chip associated with the first set of earphones; and
        creating a first composite calibration table based on the calculated correction factors for the first set of earphones to set first final adjustment factors for outputting audible test tones from the audiometer to the first set of earphones;
    performing acoustical calibration of a second set of earphones independent from the audiometer to calculate correction factors for the second set of earphones for a variety of frequencies;
    storing the calculated correction factors for the second set of earphones in an integrated circuit chip associated with the second set of earphones;
    discarding the first set of earphones and connecting the second set of earphones to the audiometer;
    reading the calculated correction factors for the second set of earphones into the audiometer from the integrated circuit chip associated with the second set of earphones; and
    creating a second composite calibration table based on the calculated correction factors for the second set of earphones to set second final adjustment factors for outputting audible test tones from the audiometer to the second set of earphones.

8. A calibrated audiometric testing system comprising:
    an audiometer having a normalized voltage level output; and
    a set of independently acoustically calibrated earphones connected to the audiometer, the earphones including an integrated circuit chip having correction factors for each ear calculated independent of the audiometer at a variety of frequencies stored thereon;
    wherein the audiometer is operable to read the correction factors from the integrated circuit chip and create a calibration table based on the correction factors to set final adjustment factors for outputting audible test tones.

9. The calibrated audiometric testing system of claim 8, wherein the integrated circuit chip further includes information related to the date and/or revision level of calibration of the earphones stored thereon.

10. The calibrated audiometric testing system of claim 8, wherein the integrated circuit chip further includes information related to where and/or by whom acoustical calibration of the earphones was performed.

11. The calibrated audiometric testing system of claim 8, wherein the integrated circuit chip further includes left and right earphone information to ensure proper connection of the earphones to the audiometer.

12. The calibrated audiometric testing system of claim 8, wherein the integrated circuit chip further includes serial number information related to the earphones.

* * * * *